United States Patent [19]

Smith et al.

[11] Patent Number: 5,196,582
[45] Date of Patent: Mar. 23, 1993

[54] PREPARATION OF SOLID QUATERNARY AMMONIUM HALIDES

[75] Inventors: Kim R. Smith; James E. Borland; Jeffrey W. Perine; Joe D. Sauer, all of Baton Rouge, La.

[73] Assignee: Ethyl Corporation, Richmond, Va.

[21] Appl. No.: 723,975

[22] Filed: Jul. 1, 1991

[51] Int. Cl.⁵ .............................................. C07C 209/12
[52] U.S. Cl. .................................. 564/292; 544/107; 544/108; 564/197; 564/282; 564/285; 564/294; 564/296
[58] Field of Search ............... 564/285, 292, 296, 197, 564/282, 294; 544/107, 108

[56] References Cited

U.S. PATENT DOCUMENTS 5,041,664  8/1991  Su ........................................ 564/296

FOREIGN PATENT DOCUMENTS 1518347  11/1969  Fed. Rep. of Germany .
0678865  10/1979  U.S.S.R. .
1144217   3/1969  United Kingdom .

Primary Examiner—Richard L. Raymond
Assistant Examiner—P. O'Sullivan
Attorney, Agent, or Firm—Patricia J. Hogan

[57] ABSTRACT

Quaternary ammonium halides are prepared in solid form by reacting an alkyl or aralkyl halide with ammonia or an amine in a liquefied gas as the solvent.

8 Claims, No Drawings

PREPARATION OF SOLID QUATERNARY AMMONIUM HALIDES

FIELD OF INVENTION

This invention relates to a process for preparing solid quaternary ammonium halides.

BACKGROUND

As shown by Morrison and Boyd, *Organic Chemistry*, 3rd Edition, Allyn and Bacon, Inc. (Boston), 1973, pp. 738-740, it is known that quaternary ammonium halides can be prepared by reacting an alkyl or aralkyl halide with ammonia or an amine in water or an alcohol as a solvent. Products prepared by such reactions have found commercial application, e.g., as biocides and cleaners, and are generally sold as 50% aqueous or 80% alcoholic solutions.

Solid quaternary ammonium halides have advantages over the solutions thereof in that they can be transported at lower costs and offer more flexibility in the formulation of products therefrom. It is possible to recover solid quaternary ammonium halides from their solutions, but it would be preferable to be able to prepare them directly in solid form.

SUMMARY OF INVENTION

It has now been found that quaternary ammonium halides can be prepared in solid form by the reaction of an alkyl or aralkyl halide with ammonia or an amine when the reaction is conducted in a liquefied gas as the solvent.

DETAILED DESCRIPTION

The alkyl or aralkyl halide which is utilized in the practice of the invention can be any of the halides already known to be useful in the preparation of quaternary ammonium halides. As indicated by Morrison and Boyd, such halides are preferably primary halides or halides which are predominantly primary halides, i.e., halides in which more than 50%, generally more than 70%, and preferably at least 90% of the molecules are primary halide molecules. The alkyl or aralkyl group may be a small or very large group but is usually a group containing up to 30 carbons, the size of the group which is preferred depending on the product which is desired.

Among the halide starting materials which can be used are the methyl, ethyl, propyl, hexyl, octyl, decyl, dodecyl, tetradecyl, hexadecyl, octadecyl, eicosyl, docosyl, tetracosyl, triacontyl, benzyl, and ethylbenzyl chlorides, bromides, and iodides, and mixtures thereof.

The nitrogen compound with which the alkyl or aralkyl halide is reacted may be ammonia or a primary, secondary, or tertiary amine. Of these nitrogen compounds, ammonia is apt to be least preferred because of (1) its requiring the greatest number of steps to be converted to a quaternary ammonium halide and (2) its necessitating the use of a mixture of alkyl or aralkyl halides and/or the use of a normally gaseous amine as the liquefied gas solvent when the desired product is a quaternary ammonium halide having different organic groups attached to nitrogen. An advantage that could be found in using ammonia as the nitrogen compound is its being a liquefiable gas which can also serve as the solvent for the reaction, although it usually would not be preferred to use ammonia as the sole liquefied gas solvent when it is also the nitrogen compound reactant.

Primary, secondary, and tertiary amines which may be used are those in which the organic groups are aliphatic or cyclic organic groups which may be hydrocarbyl or non-hydrocarbyl in nature, e.g., alkyl, hydroxyalkyl, polyoxyethylene, alkylamidoalkyl, phenyl, or benzyl, including those in which an alkyl or hydroxyalkyl group is attached to a nitrogen which is a member of a heterocyclic ring, such as a morpholine ring. Ordinarily these organic groups contain 1-30 carbons.

As is well known, some of the aforementioned amines (i.e., methylamine, ethylamine, and dimethylamine) are normally gaseous; and it is sometimes preferred to use one or more of those amines as at least a portion of the nitrogen compound to serve the dual function of reactant and solvent. However, the amine reactants which are apt to be most preferred are the tert-amines.

Among the preferred amines for use in preparing quaternary ammonium halides are tert-amines corresponding to the formula RR'R"N in which R is a primary alkyl group containing 6-24 carbons; R' is methyl, ethyl, or 2-hydroxyethyl; and R" is independently selected from methyl, ethyl, 2-hydroxyethyl, and primary alkyl groups containing 6-24 carbons. The most preferred of these tert-amines are those in which the alkyl groups in at least a majority (ordinarily at least 70%, most preferably at least 90%) of the molecules are linear alkyl groups.

Exemplary of the preferred tert-amines are (1) the N-alkyldimethyl and N,N-dialkylmethylamines in which the alkyl groups are hexyl, octyl, decyl, dodecyl, tetradecyl, hexadecyl, octadecyl, eicosyl, docosyl, and/or tetracosyl, (2) the corresponding amines in which the methyl groups are replaced with ethyl or 2-hydroxyethyl groups, and (3) mixtures of such amines.

The liquefied gas used as the reaction medium in the process may be the liquefied form of any normally gaseous material which is suitable for use as a reactant or which is inert in the sense that it will neither prevent the reaction from occurring nor react with the product. Such normally gaseous materials include, e.g., ammonia, methylamine, ethylamine, dimethylamine, air, oxygen, carbon dioxide, nitrogen, argon, ethylene, methane, ethane, propane, butane, isobutane, trifluoromethane, tetrafluoromethane, chlorotrifluoromethane, and mixtures thereof.

As already indicated, ammonia and the amines are sometimes apt to be preferred—at least as components of the solvent—when it is desired to use a solvent which is also a reactant. Carbon dioxide is frequently preferred when it is desired to use a single liquefied gas as the solvent.

Most commonly, the liquefied gas which is employed is one that is commercially available and can simply be introduced into the reaction vessel in liquid form and maintained in liquid form by the use of pressure. However, if desired, it may be acquired in the gaseous state and introduced into the reaction vessel via a compressor to liquefy it.

Because of the greater expense involved in liquefying a gas which has a very low critical temperature, it is frequently preferred to employ as the liquefied gas a normally gaseous material which has a critical temperature that is above or not much below room temperature, generally a critical temperature of at least 0° C., preferably at least 20° C., e.g., materials such as ammonia, methylamine, ethylamine, dimethylamine, ethylene, carbon dioxide, chlorotrifluoromethane, ethane, propane, butane, and isobutane.

The process of the invention is conducted by contacting the reactants at a suitable temperature and maintaining them in contact until the reaction is substantially complete. A batch, semibatch, or continuous process may be used.

When the liquefied gas which is used is one that functions as a reactant as well as a solvent, it is present throughout the reaction. When it is a liquefied gas that serves only as a solvent, it may be present throughout the reaction, or its introduction into the reaction vessel may be delayed until it is needed to maintain stirrability of the reaction mixture.

As in conventional reactions of this type, the process of the invention may be conducted at room temperature, or elevated temperatures may be used to speed the reaction. Most commonly, the process is conducted at a temperature in the range of 20°–90° C., under a pressure sufficient to maintain the liquefied gas in the liquid state. Pressures in excess of the minimum requirements can be used if desired. Ordinarily the amount of pressure used is chosen to be consistent with conducting an economical process, usually a pressure in the range of about 4.9–8.5 MPa.

In general, the reaction may be conducted so as to have supercritical or subcritical conditions.

When the reaction has been completed, the liquefied gas is vented from the reaction vessel to permit easy recovery of a solid product without the need for the crystallization, centrifugation, and drying steps required in earlier syntheses of quaternary ammonium halides.

The invention is advantageous as an economical means of preparing solid quaternary ammonium halides which can be used in the same applications as the conventional ammonium halide solutions but which (1) can be transported less expensively and (2) offer more flexibility in the formulation of products therefrom.

What is claimed is:

1. In a process for preparing a quaternary ammonium halide by reacting an alkyl or aralkyl halide with a nitrogen compound selected from ammonia and amines, the improvement which comprises conducting the reaction in a liquefied gas as the solvent.

2. The process of claim 1 wherein the halide is a primary halide.

3. The process of claim 1 wherein the nitrogen compound is an amine.

4. The process of claim 3 wherein the amine is a tert-amine.

5. The process of claim 4 wherein the tert-amine is a compound corresponding to the formula RR'R''N in which R is a primary alkyl group containing 6–24 carbons; R' is methyl, ethyl, or 2-hydroxyethyl; and R'' is independently selected from methyl, ethyl, 2-hydroxyethyl, and primary alkyl groups containing 6–24 carbons.

6. The process of claim 1 wherein the liquefied gas is a gas which has a critical temperature of at least 0° C.

7. The process of claim 6 wherein the liquefied gas has a critical temperature of at least 20° C.

8. The process of claim 7 wherein the liquefied gas is carbon dioxide.

* * * * *